United States Patent
Ha et al.

(10) Patent No.: US 9,784,697 B2
(45) Date of Patent: Oct. 10, 2017

(54) RADIATION IMAGING DEVICE CAPABLE OF MATTER-ELEMENT INFORMATION ACQUISITION AND IMAGE BASED SELECTION

(71) Applicant: KOREA ATOMIC ENERGY RESEARCH INSTITUTE, Daejeon (KR)

(72) Inventors: Jang Ho Ha, Jeonju-si (KR); Young Soo Kim, Daejeon (KR); Han Soo Kim, Daejeon (KR); Sun Mog Yeo, Daejeon (KR)

(73) Assignee: KOREA ATOMIC ENERGY RESEARCH INSTITUTE, Daejeon (KR)

( * ) Notice: Subject to any disclaimer, the term of this patent is extended or adjusted under 35 U.S.C. 154(b) by 252 days.

(21) Appl. No.: 14/424,682

(22) PCT Filed: Dec. 6, 2012

(86) PCT No.: PCT/KR2012/010552
§ 371 (c)(1),
(2) Date: Feb. 27, 2015

(87) PCT Pub. No.: WO2014/035007
PCT Pub. Date: Mar. 6, 2014

(65) Prior Publication Data
US 2015/0241367 A1    Aug. 27, 2015

(30) Foreign Application Priority Data

Aug. 30, 2012   (KR) .................. 10-2012-0095298

(51) Int. Cl.
*G01N 23/04*    (2006.01)
*G01N 23/08*    (2006.01)
(Continued)

(52) U.S. Cl.
CPC .......... *G01N 23/201* (2013.01); *G01N 23/04* (2013.01); *G01N 23/08* (2013.01); *G01N 23/083* (2013.01);
(Continued)

(58) Field of Classification Search
CPC ...... G01N 23/04; G01N 23/046; G01N 23/08; G01N 23/083; G01N 23/087;
(Continued)

(56) References Cited

U.S. PATENT DOCUMENTS 5,103,098 A * 4/1992 Fenyves .................. G01T 1/201
250/363.03
5,323,006 A * 6/1994 Thompson ............. A61B 6/502
250/363.02

(Continued)

FOREIGN PATENT DOCUMENTS

| KR | 1020090046765 | 5/2009 |
| KR | 1020100044242 | 4/2010 |

(Continued)

OTHER PUBLICATIONS

International Search Report—PCT/KR2012/010552 dated Mar. 28, 2013.

*Primary Examiner* — Allen C. Ho
(74) *Attorney, Agent, or Firm* — Cantor Colburn LLP

(57) ABSTRACT

A radiation imaging device capable of matter-element information acquisition and image based selection comprises: a radiation source generating radiation; at least one scattering device receiving radiation which includes radiation transmitting a subject and scattered radiation and scattering the received radiation; and an imaging device receiving the radiation which includes the radiation transmitting the sub-
(Continued)

ject and the scattered radiation to measure energy and positional information so as to calculate a two-dimensional image.

6 Claims, 6 Drawing Sheets

(51) Int. Cl.
  *G01N 23/083* (2006.01)
  *G01N 23/087* (2006.01)
  *G01N 23/201* (2006.01)
  *G01N 23/20* (2006.01)
  *G01N 23/202* (2006.01)

(52) U.S. Cl.
  CPC ........... *G01N 23/087* (2013.01); *G01N 23/20* (2013.01); *G01N 23/202* (2013.01)

(58) Field of Classification Search
  CPC .. G01N 23/201; G01V 5/0016; G01V 5/0041; G01V 5/005; G01V 5/0066; A61B 6/035; A61B 6/4035; A61B 6/484
  USPC .............. 378/36, 62, 53, 54, 57, 58, 86–90; 250/363.01–363.05
  See application file for complete search history.

(56) References Cited

U.S. PATENT DOCUMENTS

| | | | |
|---|---|---|---|
| 5,374,824 A * | 12/1994 | Chaney | G01T 1/201 250/363.02 |
| 5,793,045 A * | 8/1998 | DiFilippo | G01T 1/2985 250/363.03 |
| 5,812,629 A * | 9/1998 | Clauser | A61B 6/032 378/37 |
| 5,821,541 A * | 10/1998 | Tümer | G01T 1/006 250/363.03 |
| 5,841,141 A * | 11/1998 | Gullberg | G01T 1/1642 250/363.03 |
| 5,861,627 A * | 1/1999 | Basko | G01T 1/1642 250/363.04 |
| 5,943,388 A * | 8/1999 | Tümer | G01V 5/0041 378/98.11 |
| 6,140,650 A * | 10/2000 | Berlad | G01T 1/2985 250/363.03 |
| 6,236,050 B1 * | 5/2001 | Tümer | G01T 1/006 250/363.03 |
| 6,323,492 B1 * | 11/2001 | Clinthorne | G01T 1/1644 250/363.03 |
| 6,448,560 B1 * | 9/2002 | Tümer | G01T 1/006 250/370.09 |
| 6,484,051 B1 * | 11/2002 | Daniel | G01N 23/20 250/363.03 |
| 6,628,984 B2 * | 9/2003 | Weinberg | G01T 1/2985 250/363.02 |
| 6,727,502 B1 * | 4/2004 | Matthews | G01T 1/1644 250/363.02 |
| 6,858,847 B1 * | 2/2005 | Macciocchi | G01T 1/2985 250/363.03 |
| 6,915,004 B2 * | 7/2005 | Newport | G06T 11/005 128/922 |
| 7,038,212 B2 * | 5/2006 | Wollenweber | G01T 1/2985 250/363.03 |
| 7,087,905 B2 * | 8/2006 | Murayama | G01T 1/2008 250/363.03 |
| 7,129,496 B2 * | 10/2006 | Stearns | G01T 1/2985 250/363.03 |
| 7,180,979 B2 * | 2/2007 | Momose | A61B 6/06 378/62 |
| 7,274,020 B1 * | 9/2007 | Hindi | G01T 1/20 250/363.01 |
| 7,279,683 B2 * | 10/2007 | Kuroda | G01T 7/00 250/338.4 |
| 7,321,122 B2 * | 1/2008 | Bryman | G01T 1/249 250/363.03 |
| 7,433,444 B2 * | 10/2008 | Baumann | A61B 6/032 378/145 |
| 7,453,981 B2 * | 11/2008 | Baumann | A61B 6/484 378/21 |
| 7,486,770 B2 * | 2/2009 | Baumann | A61B 6/032 378/145 |
| 7,492,871 B2 * | 2/2009 | Popescu | A61B 6/00 378/145 |
| 7,522,698 B2 * | 4/2009 | Popescu | A61B 6/032 378/19 |
| 7,522,708 B2 * | 4/2009 | Heismann | A61B 6/00 378/145 |
| 7,532,704 B2 * | 5/2009 | Hempel | A61B 6/032 378/145 |
| 7,535,986 B2 * | 5/2009 | Hempel | A61B 5/02007 378/4 |
| 7,564,941 B2 * | 7/2009 | Baumann | A61B 6/484 378/146 |
| 7,639,786 B2 * | 12/2009 | Baumann | A61B 6/484 378/145 |
| 7,646,843 B2 * | 1/2010 | Popescu | A61B 6/032 356/521 |
| 7,746,981 B2 * | 6/2010 | Takahashi | G01T 1/2928 250/370.11 |
| 7,778,452 B2 * | 8/2010 | Jan | G06T 11/006 250/363.03 |
| 7,889,838 B2 * | 2/2011 | David | A61B 6/4233 378/36 |
| 7,920,673 B2 * | 4/2011 | Lanza | G02B 27/52 378/62 |
| 7,924,973 B2 * | 4/2011 | Kottler | G01B 15/025 378/36 |
| 7,945,018 B2 * | 5/2011 | Heismann | A61B 6/032 378/145 |
| 7,949,095 B2 * | 5/2011 | Ning | A61B 6/032 378/4 |
| 7,983,381 B2 * | 7/2011 | David | A61B 6/032 378/4 |
| 7,995,707 B2 | 8/2011 | Rothschild et al. | |
| 8,005,185 B2 * | 8/2011 | Popescu | A61B 6/06 378/19 |
| 8,009,796 B2 * | 8/2011 | Popescu | A61B 6/032 378/19 |
| 8,041,004 B2 * | 10/2011 | David | A61B 6/484 378/36 |
| 8,073,099 B2 * | 12/2011 | Niu | A61B 6/00 378/36 |
| 8,131,041 B2 * | 3/2012 | Ter Mors | G06T 15/08 382/131 |
| 8,139,711 B2 * | 3/2012 | Takahashi | A61B 6/00 356/457 |
| 8,183,531 B2 * | 5/2012 | Chinn | G01T 1/2985 250/252.1 |
| 8,183,535 B2 | 5/2012 | Danielsson et al. | |
| 8,184,771 B2 * | 5/2012 | Murakoshi | G01N 23/20075 378/145 |
| 8,280,000 B2 * | 10/2012 | Takahashi | A61B 6/484 378/62 |
| 8,306,183 B2 * | 11/2012 | Koehler | A61B 6/00 378/36 |
| 8,354,648 B2 * | 1/2013 | Laurent | G01T 1/295 250/363.04 |
| 8,374,309 B2 * | 2/2013 | Donath | A61B 6/032 378/145 |
| 8,515,011 B2 * | 8/2013 | Mundy | A61N 5/1048 378/65 |
| 8,565,371 B2 * | 10/2013 | Bredno | A61B 6/032 378/9 |
| 8,576,983 B2 * | 11/2013 | Baeumer | G21K 1/06 378/145 |
| 8,632,247 B2 * | 1/2014 | Ishii | A61B 6/00 378/207 |

(56) References Cited

U.S. PATENT DOCUMENTS

| | | | | |
|---|---|---|---|---|
| 8,755,487 B2* | 6/2014 | Kaneko | .................... | A61B 6/06 378/36 |
| 8,767,915 B2* | 7/2014 | Stutman | ................. | G01N 23/04 378/156 |
| 8,767,916 B2* | 7/2014 | Hashimoto | .......... | A61B 6/4291 378/62 |
| 8,781,072 B2* | 7/2014 | Robinson | ............. | G01N 23/087 378/88 |
| 8,908,824 B2* | 12/2014 | Kondoh | .................... | G01D 5/38 359/11 |
| 2008/0219540 A1 | 9/2008 | Ter Mors | | |
| 2011/0305318 A1 | 12/2011 | Robinson | | |
| 2012/0140887 A1 | 6/2012 | Mundy et al. | | |

FOREIGN PATENT DOCUMENTS

| | | |
|---|---|---|
| KR | 1020110126645 | 11/2011 |
| WO | 2004024002 | 3/2004 |

\* cited by examiner (A)

(B)

RADIATION IMAGING DEVICE CAPABLE OF MATTER-ELEMENT INFORMATION ACQUISITION AND IMAGE BASED SELECTION

TECHNICAL FIELD

The present invention relates to a radiation imaging device capable of matter-element information acquisition and image based selection.

Generally, among nondestructive inspection technologies which may find out internal states such as defects which may not be found in appearance until an object is destructed, a technology of reading an image obtained by irradiating radiation to the subject and then photosensitizing a film as much as a dose of radiation transmitting the subject is referred to as radiography.

The typical radiography can only figure out discontinuity inside a subject such as cracks and defects of a welded portion, foreign matters, and the like, but as an elaborate inspection technology is gradually developed, the radiography has been developed to be able to inspect fine defects or corrosion. For example, to determine whether there are damages such as crack in a turbine of a jet engine of aircraft, the radiography has been used like periodically performing gamma-radiography using Ir-192 gamma rays or X-rays, and the like. Alternatively, the radiography has been used to investigate an internal structure of cultural assets and photograph gold letters engraved on an excavated iron sword without damaging them. Further, the radiography has been used to check an inside of plastic products, a priming power inside of a bomb, and a solid fuel filling state of a rocket. In this case, a technology of increasing resolution using neutron having hydrogen scattering larger than an electromagnetic wave such as X-rays and gamma rays has been used. As such, the radiography technology has been used in various fields such as evaluation of integrity of large structures such as an atomic power generator and a ship and evaluation of non-uniformity of an internal state of micro parts such as a semiconductor matter. As a gamma ray source therefor, sealed sources such as Ir-192, Co-60, and Cs-137 have been used.

Recently, the radiography technology may indirectly check physical properties such as strength, phase change, and toughness of a matter itself and applications of the radiography technology are expanded, and as a result, the radiography technology has been used for life science, genetics, immunology, and the like. An absorption coefficient of radiation is changed depending on a density, a crystal structure, and a thickness of a matter of a subject, and thus transmitting power is changed, in which the absorption coefficient of radiation is proportional to the density and a linear attenuation coefficient is changed depending on a phase or a state of the matter itself. Further, these may also be changed depending on constituent components of the matter of the subject. Optical absorption characteristics of the radiation appear as an image, and therefore may be read. Ultrafine semiconductor products, high-quality products, drug, explosive powder, and the like may be read by using the foregoing characteristics.

Even in the inspection using the existing X-rays or gamma rays, special inspection technologies such as an image processing technology and a real-time digital technology have been developed and applied to the scene. A fusion image of neutron, X-rays, and gamma rays provides a clearer image and a micro focal X-ray device which is advantageous in obtaining a precision image for micro defects has been commercialized. The image is also digitalized by using an image plate or a flat semiconductor detector, not using the existing film to innovate the processing of the image or information transmission. Further, a computed tomography (CT) device which has been mainly used for a medical service due to size and cost problems of the device has been gradually used for industries. The typical nondestructive inspection technology using radiation is only to obtain a simple plane image, but recently, more elaborate image processing techniques are mobilized to keep pace with various demands and the radiography technology to obtain an original image is also advanced for use of plural-energy X-rays or neutron, scattered radiation imaging, and the like.

BACKGROUND ART

As described above, in the typical nondestructive inspection using radiation, to obtain a two-dimensional image, the radiography has been generally used and to obtain a three-dimensional image, a stereography illusion technology based on a plurality of radiation generators has been used. Describing in detail, a method for arranging a plurality of small radiation detectors and combining scanned results while conveying an object by a conveyer belt, and the like to reconfigure the combined results into a two-dimensional or three-dimensional image, and the like has been used. As such, industrial and medical imaging devices which are being commercialized perform helical and linear scanning based on a one-dimensional image to implement the two-dimensional or three-dimensional image. Meanwhile, as described above, to distinguish components of an element of a subject, a technology of irradiating plural radiation having different energy to an object to be inspected using a difference in transmitting power depending on the radiation energy to distinguish between organic matter and inorganic matters, and the like has been implemented.

International Patent Laid-Open Publication No. WO04/024002 ("SPIRAL CT DEVICE" Jan. 5, 2006) discloses a spiral CT device which includes a conical radiation source having three-dimensional diffusion, a scanner main body having a two-dimensional radiation detector detecting radiation, and the like. Further, U.S. Patent Laid-Open Publication No. 20080219540 ("System and Method for Selective Blending of 2D X-Ray Images and 3D Ultrasound Images", Sep. 11, 2008, which corresponds to U.S. Pat. No. 8,131, 041, issued on Mar. 6, 2012) discloses a system and a method for simultaneously imaging a structure using a two-dimensional X-ray image and a three-dimensional ultrasonic image and mixing the images as a single mixed two-dimensional image. Further, Korean Patent Laid-Open Publication No. 2009-0046765 ("Method and apparatus for three-dimensional imaging of object configuration", May 11, 2009) discloses a technology of counting Compton scattering of radiation by an object to perform three-dimensional scanning while analyzing constituent elements of the object and obtaining the three-dimensional image of the configuration of elements of the object based on the same.

By the way, the typical radiation image technology has a problem in that there is a limitation in image resolution or detection efficiency due to a structural problem of a method which is used to obtain the three-dimensional image. In addition, the related art needs to use radiation having plural energy, not having single energy, to distinguish elements of a subject, and therefore the device has a complex configuration and is non-economic.

DISCLOSURE

Technical Problem

An object of the present invention is to provide a radiation imaging device capable of matter-element information acquisition and image based selection by acquiring an image using both radiation and an inter-matter interaction methods to thereby improve image resolution and detection efficiency. Another object of the present invention is to provide a radiation imaging device capable of matter-element information acquisition and image based selection by particularly using a single-photon three-dimensional tracking technique to thereby acquire a three-dimensional image even with a single-energy radiation resource and simultaneously distinguish an element of a subject.

Technical Solution

In one general aspect, a radiation imaging device 100 capable of matter-element information acquisition and image based selection, includes: a radiation source 110 generating radiation; at least one scattering device receiving radiation which includes radiation transmitting a subject and scattered radiation and scattering the received radiation; and an imaging device 140 receiving the radiation which includes the radiation transmitting the subject and the scattered radiation to measure energy and positional information so as to calculate a two-dimensional image. The radiation imaging device 100 may include at least two scattering devices, that is, a first scattering device 120 and a second scattering device 130.

The radiation imaging device 100 may measure lost energy and positional information of the radiation which includes the radiation transmitting the at least one scattering device and the scattered radiation and calculate a three-dimensional image and element information of the subject by using the lost energy and energy or positional information value which are measured by the at least one scattering device and the imaging device. The radiation imaging device 100 may calculate the three-dimensional image and the element information by using a single-photon three-dimensional tracking technique based on particulate property of the radiation.

The radiation source 110 may be configured to generate at least one radiation selected from gamma rays, X-rays, electron rays, proton beam, heavy ion beam, and neutron rays.

The imaging device 140 may be formed in a pixel type to acquire the two-dimensional image.

In another general aspect, a radiation imaging method capable of matter-element information acquisition and image based selection, includes: an incident step of making radiation generated from a radiation source 110 be incident on a subject 500 and separating the incident radiation into transmitted radiation and scattered radiation; a first scattering step of making radiation including radiation transmitting the subject and the scattered radiation be incident on a first scattering device 120 and separating the incident radiation into the transmitted radiation and the scattered radiation and measuring, by the first scattering device 120, lost energy and positional information of the radiation; a second scattering step of making the radiation including the radiation transmitting the first scattering device 120 and the scattered radiation be incident on a second scattering device 130 and separating the incident radiation into the transmitted radiation and the scattered radiation and measuring, by the second scattering device 130, the lost energy and the positional information of the radiation; and a two-dimensional image acquiring step of making the radiation including the radiation transmitting the second scattering device 130 and the scattered radiation be incident on the imaging device 140 to measure, by the imaging device 140, energy and positional information of the radiation so as to calculate a two-dimensional image.

The radiation imaging device 100 may further include: a three-dimensional image acquiring step of calculating, by the imaging device 140, a three-dimensional image and element information of the subject 500 by using the lost energy and energy or positional information value which are measured by the first scattering device 120, the second scattering device 130, and the imaging device 140. The radiation imaging method may calculate the three-dimensional image and the element information by using a single-photon three-dimensional tracking technique based on particulate property of the radiation.

Advantageous Effects

The related art may obtain only the two-dimensional radiography image using a radiography technology, but according to the exemplary embodiments of the present invention, it is possible to obtain the three-dimensional image while obtaining the two-dimensional radiography image using the single-photon three-dimensional tracking technique to thereby selectively or simultaneously obtain the two-dimensional and three-dimensional images at a time by using the radiation imaging device which is configured as a single device. In particular, according to the exemplary embodiments of the present invention, it is possible to obtain the two-dimensional radiography image and the three-dimensional image and simultaneously find out the matter-element component.

BEST MODE

Figure 1:
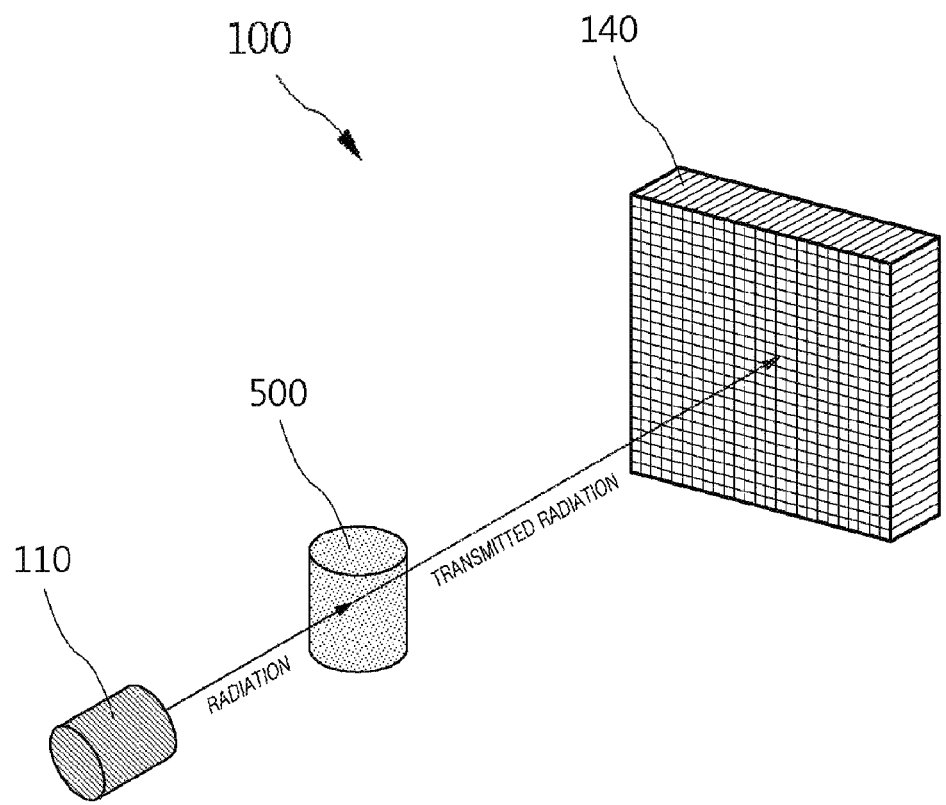
FIG. 1 is a diagram illustrating a two-dimensional image acquisition principle.

Hereinafter, a radiation imaging device 100 capable of matter-element information acquisition and image based selection having a configuration as described above will be described in detail with reference to the accompanying drawings.

As described above, the typical radiation imaging device may obtain only a two-dimensional image or does not have sufficient image resolution or detection efficiency even though it obtains a three-dimensional image and therefore may be hardly commercialized. The exemplary embodiment of the present invention proposes a radiation imaging device which may apply a single-photon three-dimensional tracking technique which may be used in radiation having high energy (which may not be applied in visible ray having low energy, and the like) to overcome the above problem, simultaneously obtain the two-dimensional and three-dimensional images and also acquire matter-element information.

A radiation imaging device 100 according to the exemplary embodiment of the present invention may be configured to include a radiation source 110 which generates radiation, at least one scattering device which receives radiation which includes radiation transmitting a subject 500 and scattered radiation and scatters the received radiation, and an imaging device 140 which receives the radiation which includes the radiation transmitting the subject 500 and the scattered radiation to measure energy and positional information so as to calculate a two-dimensional image. In this configuration, the radiation imaging device 100 may preferably include, at least two scattering devices, that is, a first scattering device 120 and a second scattering device 130. Briefly describing an image acquisition principle of the radiation imaging device 100 according to the exemplary embodiment of the present invention, when radiation transmits any object, some of the radiation is transmitted and some thereof is scattered, in which the radiation imaging device 100 further uses a scattering device in addition to a subject 500 to variously obtain transmitted radiation and scattered radiation to thereby obtain a two-dimensional image using information of the transmitted radiations and acquire a three-dimensional image and matter information using a technique of three-dimensionally tracking a single photon using information of scattered radiations. Hereinafter, each component will be described in detail.

The radiation source 110 generates radiation having energy higher than that of visible rays. The radiation generated from the radiation source 110 may be gamma rays, X-rays, electron rays, proton beam, heavy ion beam, neutron rays, and the like. As described above, in the case of rays having low energy such as visible rays, it is very difficult to track photons, but the exemplary embodiment of the present invention uses radiation having high energy to thereby perform three-dimensional tracking a single photon using particulate property of light.

The radiation imaging device 100 includes at least one scattering device. The radiation imaging device 100 may include only one scattering device, which involves a slight limitation (which will be described below in detail). At any rate, as described above, the radiation imaging device 100 most preferably includes at least two scattering devices, that is, a first scattering device 120 and a second scattering device 130. The first scattering device 120 and the second scattering device 130 serve to receive radiation and transmit and scatter the received radiation. Some of the radiation is transmitted while the radiation transmits a matter, and thus a direction thereof is not changed and some of the radiation reacts to atomic nucleus of a matter through which the radiation is transmitted and thus is secondarily scattered (in particular, Compton scattering) or some of the radiation secondarily generates radiation by nuclear reaction. According to the exemplary embodiment of the present invention, several information is finally calculated by measuring positional information of the scattered radiation, information of lost energy, and the like. The scattered radiation mentioned herein means radiation which keeps unique continuity of the incident radiation but has a state in which a direction, energy, momentum, and the like, which are in a dynamic state, are changed. (Radiation which is generally referred to as secondary radiation which is secondarily generated by the nuclear reaction is generated and the radiation does not have past information and therefore is not used in the present invention. Therefore, a description of the radiation will be omitted)

The limitation in the number of scattering device will be described below in more detail. When energy $E_0$ of the incident radiation is known, three-dimensional imaging may be implemented even by a system configured of one scattering device and an imaging device (absorber) which are disposed as illustrated in (A) of FIG. 3. In this case, an angle $\phi$ between the incident radiation and radiation of which the direction is changed due to the scattering may be calculated by the following Equation 1. In the following Equation 1, under the assumption that $m_e$ represents a mass of radiation particles and c represents light velocity, which is known values and $E_0$ is also a known value, and $E_1$ and $E_2$ are easily calculated with the first incident energy $E_0$ value and using a lost energy value measured by the scattering device and an energy value measured by the imaging device, thereby easily calculating an incident angle $\phi$.

$$E_0 = E_1 + E_2 \qquad \text{[Equation 1]}$$
$$\phi = \cos^{-1}\left(1 - m_e c^2 \left(\frac{1}{E_2} - \frac{1}{E_1 + E_2}\right)\right)$$

In other words, even though the $E_0$ in the above Equation 1 is unknown, if $E_1$ and $E_2$ values are known, the incident angle $\phi$ may be calculated only by the above Equation 1. However, an energy amount $E_1$ generally lost in the scattering device is relatively very small than an absorbed energy amount $E_2$, and therefore a difference in an error scale at the time of measurement is large, which is likely to lead to an error. In addition, the $E_2$ may not often be measured by some equipment. Considering these cases, when only one scattering device is included in the radiation imaging device 100, the accuracy of the calculated value of the incident angle $\phi$ may not be secured unless knowing the $E_0$ in advance.

By the way, it is impossible to know the energy $E_0$ of the incident radiation at all times. Therefore, when the incident energy $E_0$ is unknown, the three-dimensional imaging may be implemented by the system configured of two scattering device and imaging devices which are disposed as illustrated in (B) of FIG. 3. In this case, a relationship between the energy $E_0$ of the first incident radiation and the angle $\phi$ between the incident radiation and the radiation of which direction is changed due to the scattering is based on the following Equation 2. In the following Equation 2, $m_e$ represents a mass of radiation particles and c represents light velocity, which is known values and even though the $E_0$ is unknown, the $E_1$ and the $E_2$ can be calculated by using the lost energy values measured by the respective scattering devices, $\phi2$ can be calculated by using a value measured between the respective scattering devices and the relationship between the energy value measured by the imaging device 140 and the $E_0$, thereby calculating the incident angle $\phi$.

$$\phi = \qquad \text{[Equation 2]}$$

$$\cos^{-1}\left(1 - m_e c^2 \left(\frac{1}{E_0(E_1, E_2, \phi_2) - E_1} - \frac{1}{E_0(E_1, E_2, \phi_2)}\right)\right)$$

$$E_0(E_1, E_2, \phi_2) \equiv E_1 + \frac{E_2}{2} + \frac{1}{2}\sqrt{\left(E_2^2 + \frac{4m_e c^2 E_2}{(1 - \cos\phi_2)}\right)}$$

The positional information obtained by the respective scattering devices relies on the energy $E_0$ which is incident on the scattering device and the angle ϕ and therefore the positional information is in connection with the energy information. Therefore, the information on the position, the lost energy, and the scattered angle are collected, and as a result, it is possible to track the incident angle ϕ. Meanwhile, even in the case of the radiation generated at the same position, only an angle ϕ is actually known and therefore the radiation draws a circular shape (conical shape) on a space. When these cases are collected several times, several circles are met on the space and points meeting on the space become points where the radiations are generated.

Figure 3:
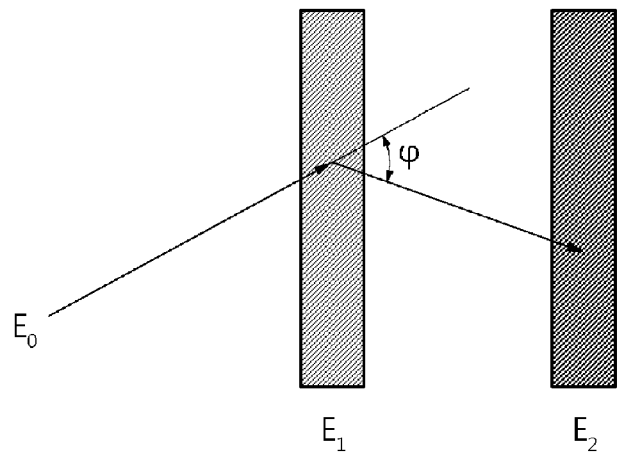
FIG. 3 is a diagram illustrating a basic principle of three-dimensional image acquisition.
Figure 3:
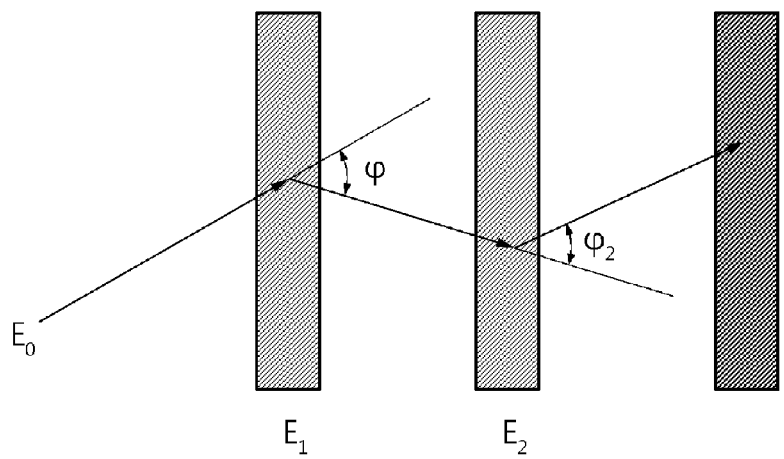

As described above, it is possible to three-dimensionally track a single photon by obtaining positional information and energy information on points passing through the scattering device using a principle which is illustrated by FIG. 3 and the above Equations 1 and 2. In particular, when the energy $E_0$ of the incident light may be appreciated as described in the above Equation 1, it is possible to track the single photon by using only one scattering device but when the energy of the incident light may not be appreciated as described in the above Equation 2, at least two scattering devices are required, but the radiation imaging device 100 according to the exemplary embodiment of the present invention may be configured to include one scattering device to track the single photon. In this case, a separate incident light energy detector is required, and therefore it is more preferable that the radiation imaging device 100 includes at least two scattering devices.

The imaging device 140 receives the radiation transmitting all of a subject 500, the first scattering device 120, and the second scattering device 130 to thereby measure the energy and the positional information. A two-dimensional radiography image of the subject 500 may be calculated by using the so measured energy and positional information. Here, the imaging device 140 not only includes an incident unit (not shown) which directly receives radiation, but also includes an operation unit (not shown) which recognizes incident position or strength, and the like and calculates image information using the recognized incident position or strength, an output unit (not shown) which displays the calculated image information, and the like. (For example, the operation unit of the imaging device 140 may be implemented as a computer, and the like and the output unit may be implemented as a monitor, and the like which is connected to the computer) In the drawings of the present invention which will be referenced in the following description, to schematically illustrate the imaging device 140, only a portion corresponding to the incident unit is illustrated, but even though not illustrated in the drawings, the imaging device 140 is configured to include the operation unit, the output unit, and the like which are described above.

In this case, the imaging device 140 may be preferably formed in a pixel type to acquire the two-dimensional image. As such, when the imaging device 140 is formed in the pixel type, the positional information may be easily obtained only by figuring out by what pixel the fact that the rays are incident is recognized and therefore an operation load at the time of calculating the image information later may be reduced.

FIG. 1 illustrates a two-dimensional image acquisition principle in a radiation imaging device 100 according to the exemplary embodiment of the present invention. In FIG. 1, since the transmitted radiation is used at the time of acquiring the two-dimensional image, the first scattering device 120 and the second scattering device 130 which are provided to generate the scattered radiation are omitted.

As illustrated in FIG. 1, when the radiation is generated from the radiation source 110 and then is incident on the subject 500, some of the radiation transmits the subject 500. In this case, when the radiation transmits any matter, the strength of the radiation after transmitting the matter is changed depending on a material or a thickness of the matter. That is, when a matter is made of a material which absorbs radiation well, a matter is thick, or the like, the strength of the transmitted radiation is weak (that is, the energy of the transmitted radiation is relatively low), but in the opposite case, the strength of the transmitted radiation is strong (that is, the energy of the transmitted radiation is relatively high, which is of course lower than the energy of radiation prior to being transmitted). Therefore, the energy and the positional information of the radiation transmitting the subject 500 are measured to thereby obtain the two-dimensional radiography image of the subject 500 using the imaging device 140.

The two-dimensional radiography image acquisition principle is similar to that of a generally used X-ray photograph and the like and therefore the detailed description thereof will be omitted.

Figure 2:
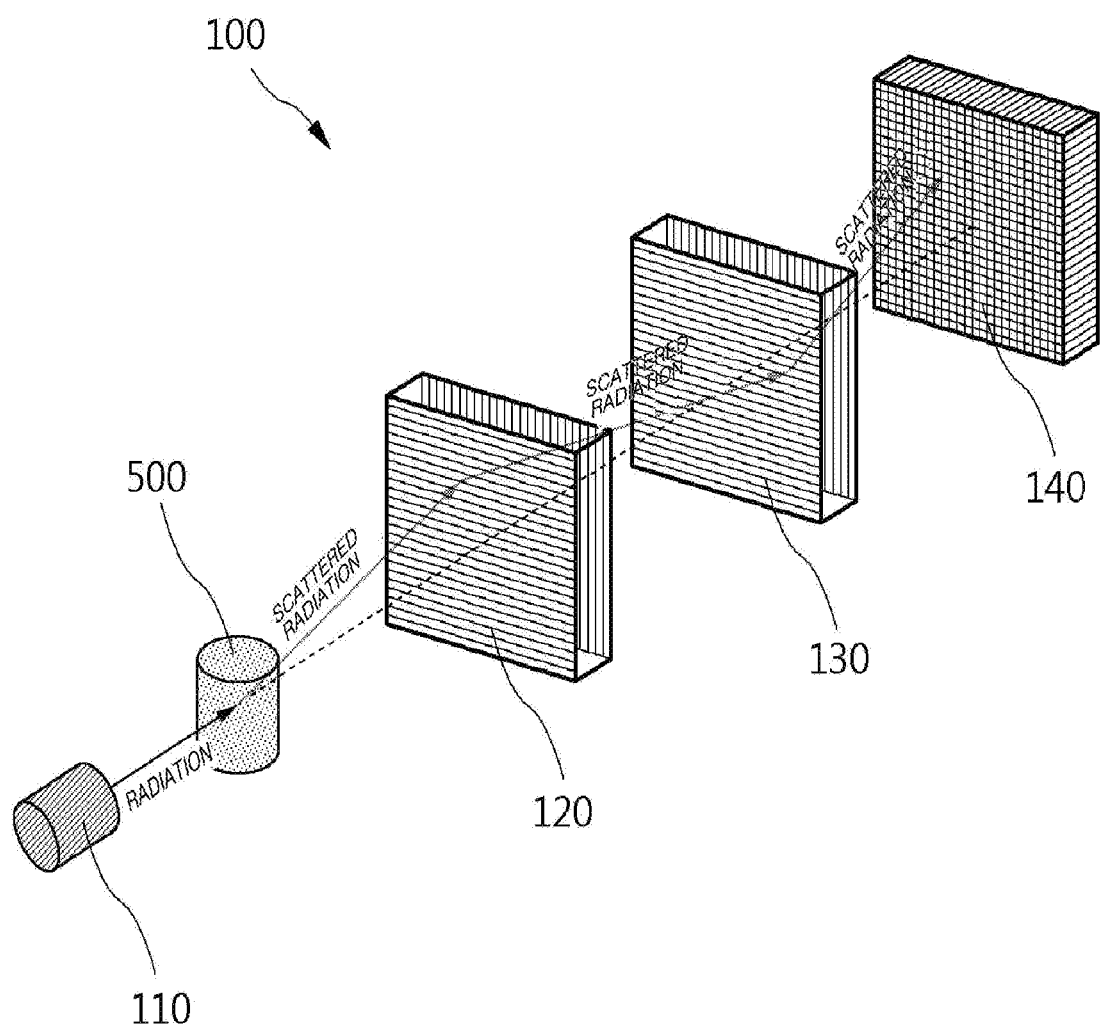
FIG. 2 is a diagram illustrating a principle of a single-photon three-dimensional tracking technique.

FIG. 2 illustrates a single-photon three-dimensional tracking technique principle in the radiation imaging device 100 according to the exemplary embodiment of the present invention. As described above, in the case of the radiation having high energy may three-dimensionally track the single photon. That is, dynamic analysis may be made using the particulate property of the radiation. According to the exemplary embodiment of the present invention, the three-dimensional image of the subject 500 is obtained.

As illustrated in FIG. 2, when the radiation is generated from the radiation source 110 and then is incident on the subject 500, some of the radiation reacts to atomic nucleus of the subject 500 and is thus secondarily scattered. As described above, the state of the scattered radiation is dynamically changed, like the partial loss of energy of the scattered radiation, the change in the direction of the scattered radiation from an original direction, and the like. Further, the scattered radiation leaves the positional information at a point where the scattered radiation meets the first scattering device 120 or the second scattering device 130, and consequently, the scattered radiation is incident on the imaging device 140 to measure the energy and the positional information.

As described above, the scattered radiation is generated by the Compton scattering while passing through the subject 500 and therefore the path change direction or the lost energy is changed depending on the matter of the subject 500. Since it is possible to measure how much the amount of energy lost in the first scattering device 120 or the second scattering device 130 is and the positions of the subject 500, the first scattering device 120, the second scattering device 130, and the imaging device 140 are known, the path of the scattered radiation may be accurately appreciated by the positional information measured by each of devices 120, 130, and 140. In particular, as described above, since the radiation has a high energy level, the tracking may be made even though the energy is lost while the scattered radiation is generated. That is, in the case of using the radiation, the single-photon three-dimensional tracking (tracking the path of the scattered radiation) may be made.

Therefore, the three-dimensional image and the matter-element information of the subject 500 may be reconfigured by a method for determining a final position of radiation by dynamics based on the particulate property of the radiation using the information (lost energy, positional information).

Figure 4:
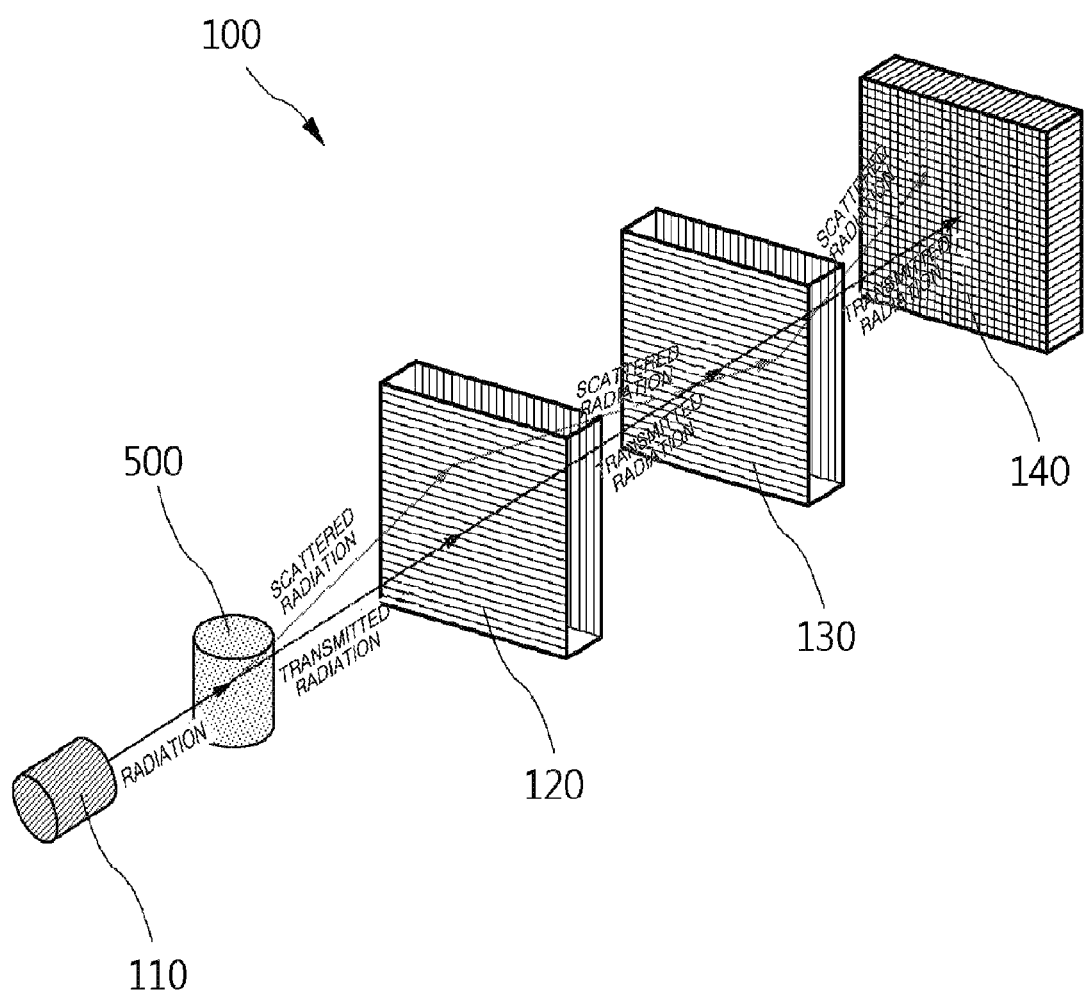
FIG. 4 is a diagram illustrating a radiation imaging device according to an exemplary embodiment of the present invention.

FIG. 4 illustrates a two-dimensional and three-dimensional image and matter-element information acquisition principle of the radiation imaging device 100 according to the exemplary embodiment of the present invention. Describing in more detail, a method for acquiring a two-dimensional radiography image using the transmitted radiation in FIG. 1 and a method for acquiring three-dimensional image and matter-element information using the scattered radiation in FIG. 2 are simultaneously used.

FIG. 1 does not illustrate the scattered radiation for simplification of drawings during the description of the two-dimensional radiography image acquisition principle, but to the contrary, FIG. 2 does not illustrate the transmitted radiation for simplification of drawing during the description of the three-dimensional image and matter-element information acquisition principle. However, in the case of in FIG. 1 or FIG. 2, the scattered radiation and the transmitted radiation which are not illustrated are actually generated and therefore when the energy, the positional information, and the like of all the radiations are integrally measured, it is possible to simultaneously acquire the two-dimensional radiography image, the three-dimensional image, and the matter-element information of the subject 500.

Figure 5:
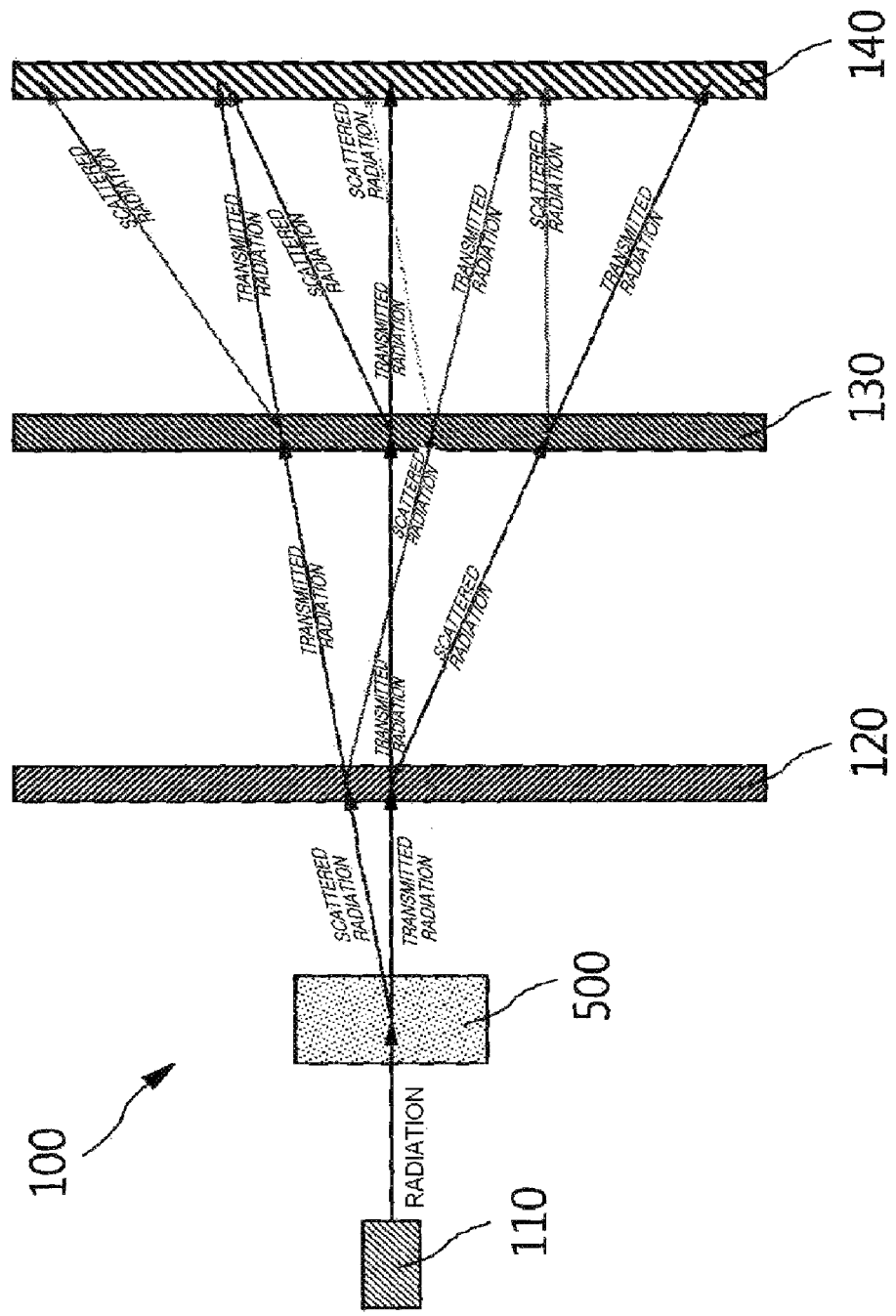
FIG. 5 is a diagram illustrating an example of a radiation propagation path in the radiation imaging device according to the exemplary embodiment of the present invention.

FIG. 5 is a diagram illustrating an example of a radiation propagation path in the radiation imaging device 100 according to the exemplary embodiment of the present invention. For explanation of each principle, any of the transmitted radiation and the scattered radiation is omitted in FIGS. 1 to 3 but the transmitted radiation and the scattered radiation are generated while the radiation transmits the subject 500, the first scattering device 120, and the second scattering device 130. Therefore, actually, both of the transmitted radiation (propagated in the same direction as a primary radiation) and the scattered radiation (propagated in a direction changed from the propagation direction of the transmitted radiation) are generated while the radiation sequentially transmits the subject 500, the first scattering device 120, and the second scattering device 130. In this case, finally, it is possible to discriminate which radiation is the transmitted radiation and which radiation is the scattered radiation by measuring the energy of radiation which reaches the imaging device 140.

A detailed description thereof will be provided below. When comparing the magnitudes in energy of the transmitted radiation and the scattered radiation which are generated while the radiation transmits a matter, it may be appreciated that the transmitted radiation absorbs energy as much as an amount absorbed by transmitting the matter and the scattered radiation is generated by a scattering reaction with the matter and therefore the transmitted radiation has energy higher than the scattered radiation. In the viewpoint, when the radiation sequentially transmits the subject 500, the first scattering device 120, and the second scattering device 130, it may be expected that the radiation which is propagated in transmission-transmission-transmission will have the highest energy and the radiation which is propagated in scattering-scattering-scattering will have the lowest energy. Further, since the three-dimensional form or the matter-element information of the subject 500 is yet unknown, a slight deviation may occur, but characteristic information on the first scattering device 120 and the second scattering device 130 is known in advance (that is, it is already known how much the energy is lost or how the direction is changed when the radiation passes through the first scattering device 120 and the second scattering device 130) and in the case of the radiation propagated in transmission-transmission-transmission, when considering that fact that the propagation direction is not changed and the fact that the radiation propagated in scattering-scattering-scattering will have the lowest energy in any case, (even though it is difficult to distinguish a similar set like the radiation propagated in [transmission-scattering-transmission]/radiation propagated in [scattering-transmission-transmission]/radiation propagated in [transmission-transmission-scattering]), it is possible to clearly distinguish between the radiation propagated in transmission-transmission-transmission and the radiation propagated in scattering-scattering-scattering at all times.

The radiation propagated in transmission-transmission-transmission in FIG. 5 is the radiation which is used in the principle of obtaining the two-dimensional radiography image illustrated in FIG. 1 or 4. Further, the radiation propagated in scattering-scattering-scattering in FIG. 5 is radiation which is used in a principle of obtaining the three-dimensional image and matter-element information illustrated in FIG. 2 or 4. As described in the description of FIG. 5, it is possible to individually recognize the radiation for obtaining the two-dimensional radiography image and the radiation for obtaining the three-dimensional image and matter-element information and therefore it is possible to obtain all of the two-dimensional radiography image alone (two-dimensional mode)/three-dimensional image and matter-element information alone (three-dimensional mode)/two-dimensional radiography image, and the three-dimensional image and matter-element information (simultaneous mode) by the radiation imaging device 100 according to the exemplary embodiment of the present invention.

As described above, the radiation imaging device 100 according to the exemplary embodiment of the present invention may simultaneously acquire the two-dimensional radiography image, the three-dimensional image, and the matter-element information in real time and therefore the use range and utilization thereof are largely expanded unlike the typical radiation imaging device.

As an example, a typical radiation imaging device cannot but confirm a treatment effect by performing CT or MRI photographing after particle beam treatment at the time of treatment of particle beam such as proton in a medical field and has inconvenience to again perform a process of again performing treatment and confirmation when the treatment is not performed properly during the process. However, the radiation imaging device 100 according to the exemplary embodiment of the present invention may know the matter-element configuration simultaneously with obtaining the two-dimensional and three-dimensional image to simultaneously perform treatment and observation so as to immediately perform the correction if necessary while confirming the treatment state in real time, thereby minimizing aftereffects of normal cells due to the radiation, and the like and performing better treatment than the related art.

A method for obtaining radiation image using the radiation imaging device 100 according to the exemplary embodiment of the present invention as described above will be described briefly.

In the radiation imaging method capable of matter-element information acquisition and image based selection according to the exemplary embodiment of the present invention, first, in the incident step, the radiation generated from the radiation source 110 is incident on the subject 500 and thus the radiation is separated into the transmitted radiation and the scattered radiation. Next, in the first scattering step, the radiation which includes the radiation transmitting the subject 500 and the scattered radiation is incident on the first scattering device 120 and thus is separated into the transmitted radiation and the scattered radiation and the first scattering device 120 measures the lost energy and the positional information of the radiation. Next, in the second scattering step, similar to the first scattering step, the radiation which includes the radiation transmitting the first scattering device 120 and the scattered radiation is incident on the second scattering device 130 and thus is separated into the transmitted radiation and the scattered radiation and the second scattering device 130 measures the lost energy and the positional information of the radiation. Next, in the two-dimensional image acquiring step, the radiation which includes the radiation transmitting the second scattering device 130 and the scattered radiation is incident on the imaging device 140 and thus the imaging device 140 measures the energy and positional information of the radiation to calculate the two-dimensional image. In this case, the radiation imaging method may further include: a three-dimensional image acquiring step of calculating, by the imaging device 140, a three-dimensional image and element information of the subject 500 by using the lost energy and energy or positional information value which are measured by the first scattering device 120, the second scattering device 130, and the imaging device 140. As described above, the three-dimensional image and element information may be calculated by using the single-photon three-dimensional tracking technique based on the particulate property of radiation.

Figure 6:
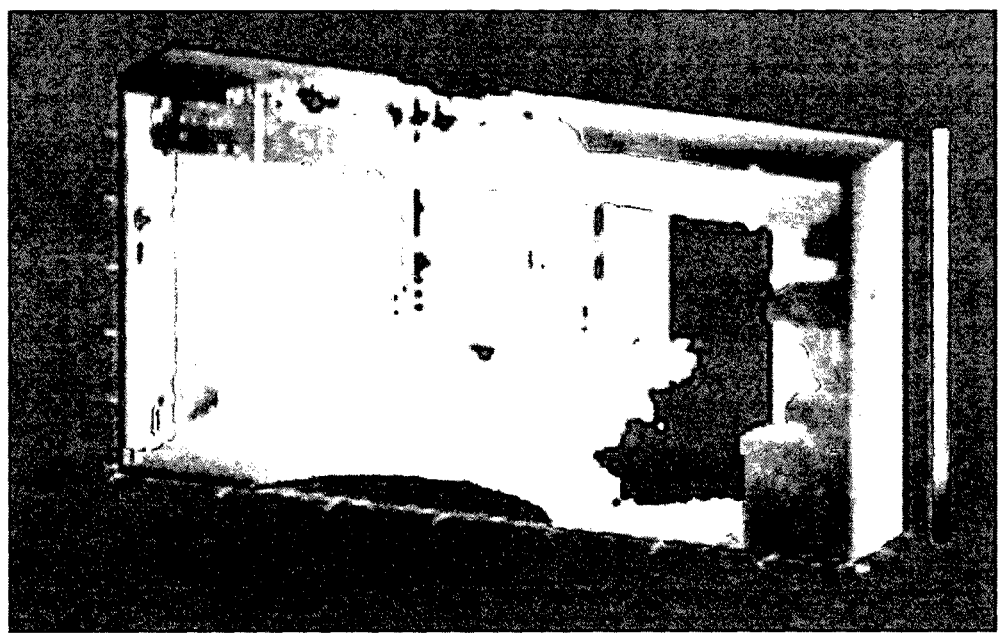
FIG. 6 is a diagram illustrating an example of a three-dimensional image calculated by the radiation imaging device according to the exemplary embodiment of the present invention.

FIG. 6 is a diagram illustrating an example of a three-dimensional image calculated by the radiation imaging device according to the exemplary embodiment of the present invention. In an example of FIG. 6, the subject 500 is an object having a large thickness like a container and as illustrated in FIG. 6, a very excellent three-dimensional image for an object having a large thickness may be obtained.

The present invention is not limited to the above-mentioned embodiments but may be variously applied, and may be variously modified by those skilled in the art to which the present invention pertains without departing from the gist of the present invention claimed in the claims.

INDUSTRIAL APPLICABILITY

When the apparatus according to the exemplary embodiment of the present invention is applied to, in particular, the medical field, the following effects may be obtained. The typical radiation imaging device cannot but confirm a treatment effect by performing CT or MRI photographing after particle beam treatment at the time of treatment of particle beam such as proton and has inconvenience to again perform a process of again performing treatment and confirmation when the treatment is not performed properly during the process. However, when the apparatus according to the exemplary embodiment of the present invention is applied to the medical field, the two-dimensional and three-dimensional images are obtained and simultaneously the matter-element configuration may be known, and therefore the treatment and observation may be simultaneously performed, thereby immediately performing the correction if necessary while confirming the treatment state in real time. Therefore, it is also possible to minimize the aftereffects of normal cells due to the radiation, and the like.

The invention claimed is:

1. A radiation imaging device capable of matter-element information acquisition and image based selection, comprising:
    a radiation source configured to generate radiation and make the radiation be incident on a subject and separate the incident radiation into first transmitted radiation and first scattered radiation;
    a first scattering device configured to separate the first transmitted radiation and the first scattered radiation incident thereon into second transmitted radiations and second scattered radiations, and measure lost energy and positional information of the radiation;
    a second scattering device configured to separate the second transmitted radiations and the second scattered radiations incident thereon into third transmitted radiations and third scattered radiations, and measure the lost energy and the positional information of the radiation; and
    an imaging device configured to calculate a two-dimensional image by using the third transmitted radiations incident thereon, the lost energy and the positional information of the radiation, and configured to calculate a three-dimensional image and element information of the subject by using the lost energy or the positional information which are measured by the first scattering device, the second scattering device, and the imaging device.

2. The radiation imaging device of claim 1, wherein the three-dimensional image and the element information are calculated by using a single-photon three-dimensional tracking technique based on particulate property of the radiation.

3. The radiation imaging device of claim 1, wherein the radiation source generates at least one radiation selected from the group consisting of gamma rays, X-rays, electron rays, proton beam, heavy ion beam, and neutron rays.

4. The radiation imaging device of claim 1, wherein the imaging device is formed in a pixel type to acquire the two-dimensional image.

5. A radiation imaging method capable of matter-element information acquisition and image based selection, comprising:
    an incident step of making radiation generated from a radiation source be incident on a subject and separating the incident radiation into first transmitted radiation and first scattered radiation;
    a first scattering step of making the first transmitted radiation and the first scattered radiation be incident on a first scattering device and separating the first transmitted radiation the first scattered radiation into second transmitted radiations and second scattered radiations, and measuring, by the first scattering device, lost energy and positional information of the radiation;
    a second scattering step of making the second transmitted radiations and the second scattered radiations be incident on a second scattering device and separating the second transmitted radiations and the second scattered radiations into third transmitted radiations and third scattered radiations, and measuring, by the second scattering device, the lost energy and the positional information of the radiation;

a two-dimensional image acquiring step of making the third transmitted radiations and the third scattered radiations be incident on an imaging device to measure, by the imaging device, the lost energy and the positional information of the radiation so as to calculate a two-dimensional image; and a three-dimensional image acquiring step of calculating, by the imaging device, a three-dimensional image and element information of the subject by using the lost energy or the positional information, which are measured by the first scattering device, the second scattering device, and the imaging device.

6. The radiation imaging method of claim 5, wherein the three-dimensional image acquiring step comprises calculating the three-dimensional image and the element information using a single-photon three-dimensional tracking technique based on particulate property of the radiation.

* * * * *